(12) United States Patent
Christenson

(10) Patent No.: US 8,608,729 B2
(45) Date of Patent: Dec. 17, 2013

(54) IMPLANTABLE INFUSION DEVICE HAVING FILTER

(75) Inventor: Steven R. Christenson, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 1177 days.

(21) Appl. No.: 12/105,441

(22) Filed: Apr. 18, 2008

(65) Prior Publication Data
US 2009/0264870 A1 Oct. 22, 2009

(51) Int. Cl.
*A61K 9/22* (2006.01)

(52) U.S. Cl.
USPC .................................................. 604/891.1

(58) Field of Classification Search
USPC ........ 604/890.1, 891.1, 892.1, 131–132, 140, 604/146, 151–152, 93.01, 288.01–288.04
See application file for complete search history.

(56) References Cited

U.S. PATENT DOCUMENTS

| | | | |
|---|---|---|---|
| 3,951,147 A * | 4/1976 | Tucker et al. | 604/891.1 |
| 4,360,019 A * | 11/1982 | Portner et al. | 604/131 |
| 4,482,346 A | 11/1984 | Reinicke | |
| 4,486,190 A | 12/1984 | Reinicke | |
| 4,573,994 A * | 3/1986 | Fischell et al. | 604/891.1 |
| 4,692,147 A | 9/1987 | Duggan | |
| 4,838,887 A | 6/1989 | Idriss | |
| 5,049,141 A | 9/1991 | Olive | |
| 5,137,529 A * | 8/1992 | Watson et al. | 604/891.1 |
| 5,306,255 A * | 4/1994 | Haindl | 604/175 |
| 5,417,663 A | 5/1995 | Slettenmark | |
| 5,527,307 A * | 6/1996 | Srisathapat et al. | 604/892.1 |
| 5,643,207 A | 7/1997 | Rise | |
| 5,695,490 A * | 12/1997 | Flaherty et al. | 604/891.1 |
| 5,770,076 A * | 6/1998 | Chu et al. | 210/490 |
| 5,957,890 A | 9/1999 | Mann et al. | |
| 6,013,051 A | 1/2000 | Nelson | |
| 6,039,712 A * | 3/2000 | Fogarty et al. | 604/288.02 |
| 6,997,921 B2 | 2/2006 | Gray | |
| 7,186,236 B2 | 3/2007 | Gibson | |
| 7,255,690 B2 * | 8/2007 | Gray et al. | 604/891.1 |
| 2003/0216714 A1 | 11/2003 | Gill | |

OTHER PUBLICATIONS

PCT Search Report dated Jun. 5, 2009.

* cited by examiner

*Primary Examiner* — Kevin C Sirmons
*Assistant Examiner* — William Carpenter
(74) *Attorney, Agent, or Firm* — Mueting Raasch & Gebhardt PA

(57) ABSTRACT

An implantable infusion device for delivering a fluid medication to a patient. The infusion device has an internal bacterial filter positioned between the reservoir and the pump, configured to provide a pathway for fluid to be pulled from the reservoir to the pump, regardless of the orientation of the infusion device. The configuration of the filter provides a fluid pathway from the reservoir to the pump, even in the presence of a gas bubble.

3 Claims, 7 Drawing Sheets

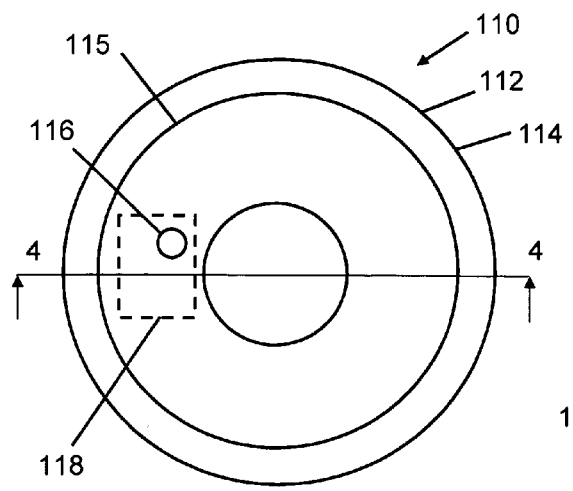
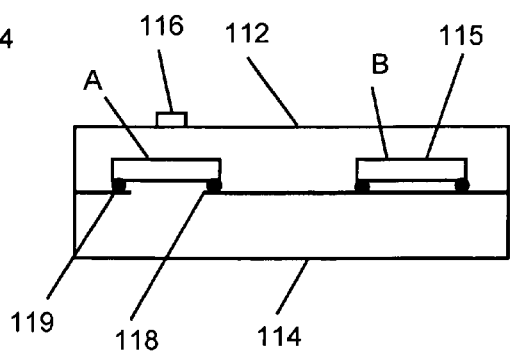
FIG. 4A
FIG. 4B
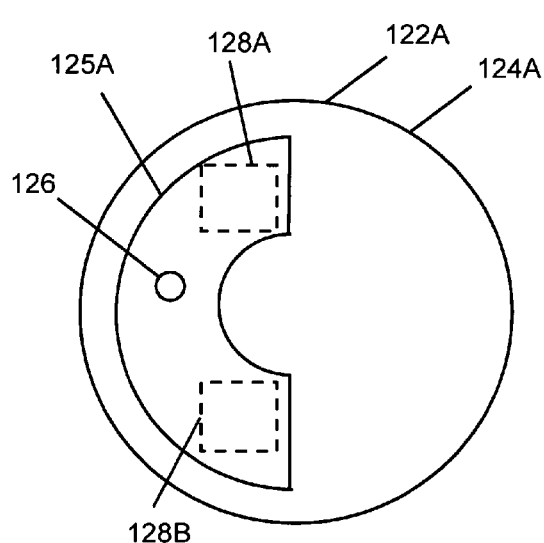
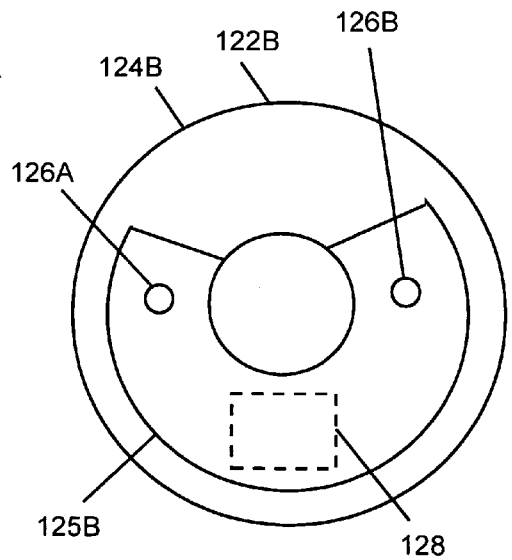
FIG. 5A
FIG. 5B

IMPLANTABLE INFUSION DEVICE HAVING FILTER

FIELD OF THE INVENTION

The present disclosure is directed to medical devices, systems and methods associated therewith, more particularly, to implantable infusion pumps. The devices of this disclosure are more specifically implantable infusion devices having a pump and a bacterial filter.

BACKGROUND OF THE INVENTION

Implantable infusion devices are well known in the art and have been used to treat a variety of conditions or diseases such as pain, spasticity, and cancer. These infusion devices typically include a liquid medication reservoir within a housing or bulkhead. Some form of fluid flow control is also provided to control or regulate the flow of fluid medication from the reservoir to the outlet of the device for delivery of the medication to the desired location in a body, usually through a catheter.

Active drug infusion devices feature a pump or a metering system to deliver the drug into the system of a patient. An example of such a drug infusion pump currently available is the Medtronic SynchroMed programmable pump. Such devices typically include a drug reservoir, a fill port, a pump to pump out the drug from the reservoir, and a catheter port to transport the drug from the reservoir via the pump to a patient's anatomy. The drug reservoir, fill port, pump, and catheter port are generally held in a housing, or bulkhead.

The bulkhead typically has a series of passages extending from the drug reservoir and through the pump that lead to the catheter port, which is typically located on the side of the bulkhead. The drug is pumped through a catheter connected to the catheter port, and is delivered to a targeted patient site from a distal end of the catheter.

Often, a bacterial filter is present within the infusion device to filter the drug prior to being expressed into the patient. In some device designs, the filter is positioned between the reservoir and the pump.

Various types of implantable infusion devices are known. Two common classes of infusion devices are positive pressure (where the pressure in the reservoir is positive in relation to its surrounding volume in the bulkhead) and negative pressure (wherein the pressure in the reservoir is negative or neutral to its surrounding volume in the bulkhead). A positive pressure reservoir may be provided by a pressurizing means so that the contents of the reservoir are continuously pressurized. The pressurizing means may simply be a spring loaded actuator acting on a flexible bag type reservoir or may incorporate pressurized gas on flexible metal reservoir, or a resilient bag to constantly maintain the contents of the reservoir under pressure. Examples of positive pressure infusion devices are typified by U.S. Pat. No. 4,838,887 (Idriss), U.S. Pat. No. 5,049,141 (Olive) and U.S. Pat. No. 7,255,690 (Gray et al.). For a negative pressure or neutral device, the reservoir is not pressurized, but rather, the drive mechanism draws the fluid from the reservoir. In some devices, the drive mechanism uses electromagnetic and mechanical forces to move a piston between retracted and forward positions, thus drawing the fluid medication from the reservoir, through an inlet and forcing it out an outlet. An exemplary drive mechanism of this type is disclosed in U.S. Pat. No. 6,997,921 (Gray). With a negative or neutral pressure reservoir, the liquid must be drawn out of the reservoir and into the drive mechanism in order to prime the drive mechanism. This requires that the drive mechanism include features for drawing the fluid medication from the reservoir and through a flow path to the outlet chamber rather than receiving the fluid medication via positive pressure. Examples of negative pressure infusion devices are typified by U.S. Pat. No. 4,482,346 (Reinicke) and U.S. Pat. No. 4,486,190 (Reinicke).

BRIEF SUMMARY OF THE INVENTION

The present disclosure is directed to implantable infusion devices for delivering a fluid medication, such as a drug, medicament or other therapeutic agent, to a patient. The infusion device has an internal bacterial filter positioned in the fluid flow between the reservoir and the pump, configured to filter fluid from the reservoir prior to reaching the pump inlet. The filter also provides an alternate path for fluid to be pulled from the fluid reservoir to the pump, regardless of the orientation of the infusion device. The configuration of the filter allows fluid to pass from the reservoir to the pump, even in the presence of gas bubble(s). In some embodiments, the device is an implantable negative pressure infusion device.

In a first aspect, this disclosure is directed to an implantable infusion device that has a reservoir having an interior and an outlet, with the interior having a pressure of no more than about 5 psig. A bulkhead in fluid communication with the reservoir houses a pump having an inlet and also houses a fluid flow path from the reservoir to the pump inlet. A bacterial filter extends across the fluid flow path between the reservoir and the pump inlet, the bacterial filter extending at least about 180 degrees, in some embodiments at least about 270 degrees, or 360 degrees. The reservoir could have a neutral or negative pressure therein, making the device a neutral or negative pressure infusion device. The bacterial filter could be composed of a plurality of individual filter elements in fluid connection with each other, that extend at least about 180 degrees, in some embodiments at least about 270 degrees, or 360 degrees.

In a second aspect, this disclosure is directed to an implantable infusion device, such as a negative pressure infusion device, a neutral pressure infusion device, or a slightly positive pressure infusion device, having a reservoir and a bulkhead, the bulkhead housing a pump having an inlet and also housing a fluid flow path from the reservoir to the pump. A bacterial filter extends across the fluid flow path from the reservoir to the pump, the filter being configured to inhibit air lock of the device. The bacterial filter could extend at least about 180 degrees, at least about 270 degrees or 360 degrees. The bacterial filter could be composed of a plurality of individual filter elements in fluid connection with each other, that extend at least about 180 degrees, in some embodiments at least about 270 degrees, or 360 degrees.

In a third aspect, this disclosure is directed to an implantable infusion device having a reservoir and a bulkhead housing a pump having an inlet and also housing a fluid flow path from the reservoir to the pump. A bacterial filter extends across the fluid flow path from the reservoir to the pump, the filter comprising a plurality of filter elements arranged in an annular shape and in fluid communication with each other. The reservoir could have a neutral, negative pressure, or slightly positive pressure therein, making the device a neutral infusion device, a negative pressure infusion device, or a slightly positive pressure device.

The above summary of the present disclosure is not intended to describe each illustrated or described embodiment of this disclosure. The following figures and detailed description more particularly exemplify these embodiments.

BRIEF DESCRIPTION OF THE DRAWINGS

FIG. 4A is a schematic top view of a first embodiment of a portion of an infusion device having an annular filter according to this disclosure. FIG. 4B is a schematic cross-sectional side view the infusion device of FIG. 4A, taken along line 4-4.

FIG. 5A is a schematic top view of a first embodiment of a portion of an infusion device having a semi-annular filter according to this disclosure.

FIG. 5B is a schematic top view of a second embodiment of a portion of an infusion device having a semi-annular filter according to this disclosure.

DETAILED DESCRIPTION OF THE INVENTION

The invention of this disclosure may be embodied in various forms. In the following detailed description, reference is made to the accompanying drawings that form a part hereof, and in which are shown by way of illustration several specific embodiments of infusion devices, systems and methods. It is to be understood that other embodiments are contemplated and may be made without departing from the scope or spirit of the present invention. The following detailed description, therefore, is not to be taken in a limiting sense.

Figure 1:
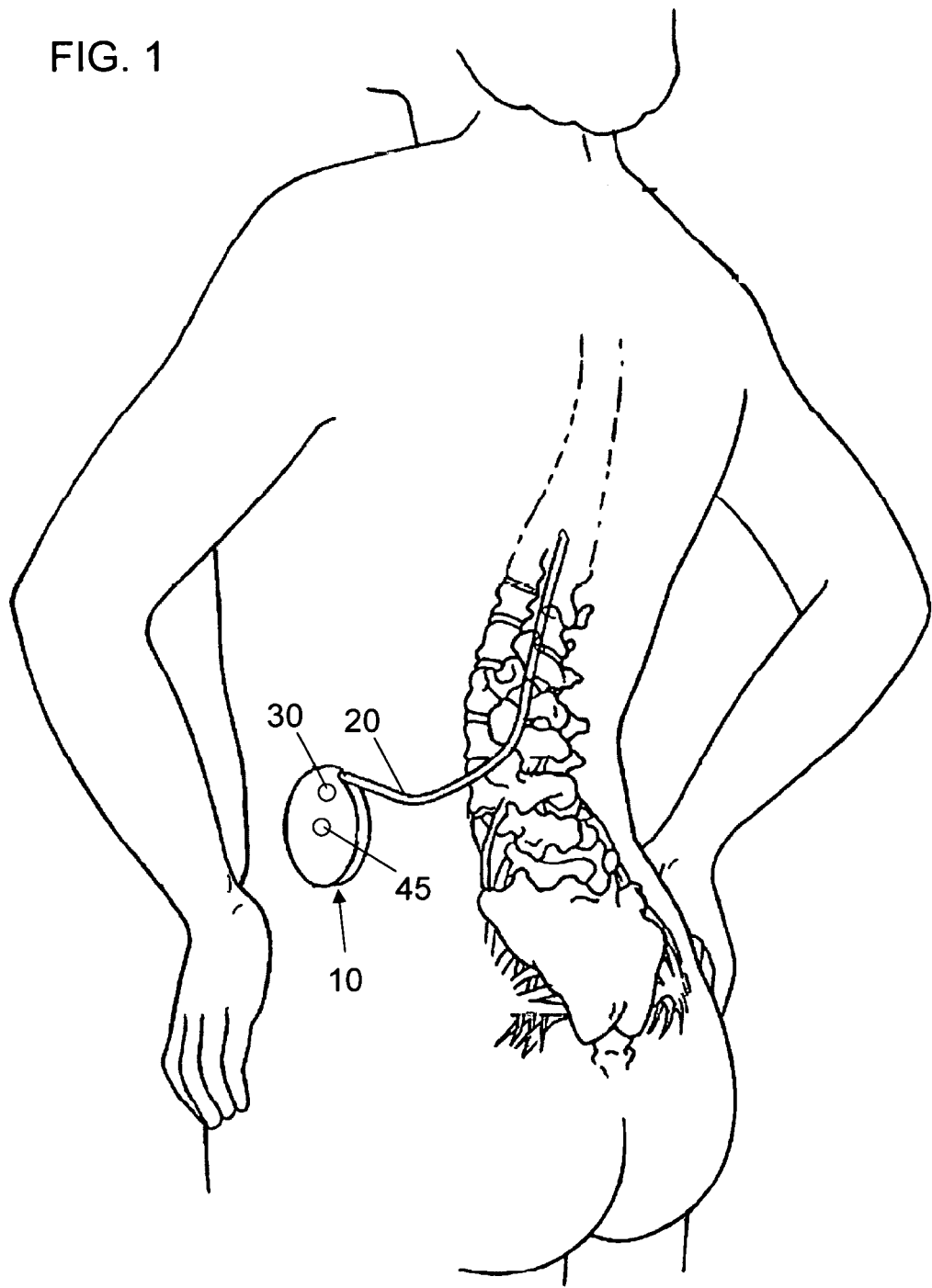
FIG. 1 is a schematic representation of a perspective view of an infusion system implanted in a patient.

Referring to FIG. 1, a general representative environment for an implanted system, in this embodiment an infusion device 10 and associated device 20, is shown. In this figure, infusion device 10 is subcutaneously implanted in an abdominal region of a patient. Operably connected to infusion device 10 is an associated device 20 for transmitting fluid medication from device 10 to the patient. A distal portion of device 20 is intrathecally inserted into the patient's spinal canal through a lumbar puncture and advanced rostrally to a desired location. Proximal end of associated device 20 is tunneled subcutaneously to the location of infusion device 10, where it may be connected to device 10. While distal portion of associated device 20 is shown in FIG. 1 as being located in or on the spinal cord, it will be understood that associated device 20 may be placed at any location in the patient for which it is desirable to administer fluid medication delivered by infusion device 10.

In the embodiment shown in FIG. 1, associated device 20 is a catheter operably connected to infusion device 10. Catheter 20 is typically a flexible tube with a lumen running from the proximal end of catheter 20 to one or more delivery regions that are typically located at the distal portion of catheter 20. Proximal portion of catheter 20 is connected to infusion device 10. Distal portion of catheter 20 is positioned at a target location in the patient to deliver fluid medication from infusion device 10 to the patient through a delivery region of catheter 20. Device 10 includes a reservoir (not shown in FIG. 1) for housing a fluid medication and a refill port 45 in fluid communication with reservoir. The reservoir may be refilled by percutaneously inserting a needle (not shown) into the patient such that needle enters refill port 45, and fluid medication may be delivered into the reservoir from the needle via refill port 45. Infusion device 10 shown in FIG. 1 also includes an access port 30 in fluid communication with catheter 20. Fluid may be injected into or withdrawn from the patient through catheter 20 via catheter access port 30 by percutaneously inserting a needle into access port 30.

Figure 2A:
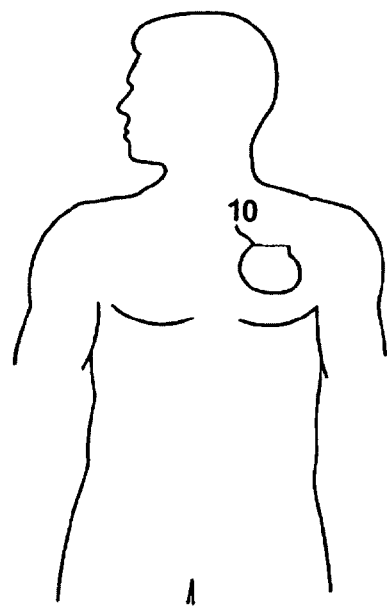
FIGS. 2A-D are schematic representations of plan views of infusion systems implanted in various locations in patients.
Figure 2B:
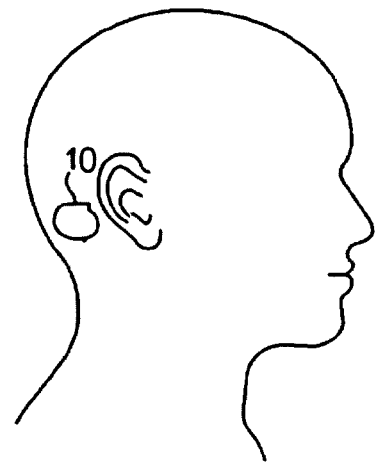
Figure 2C:
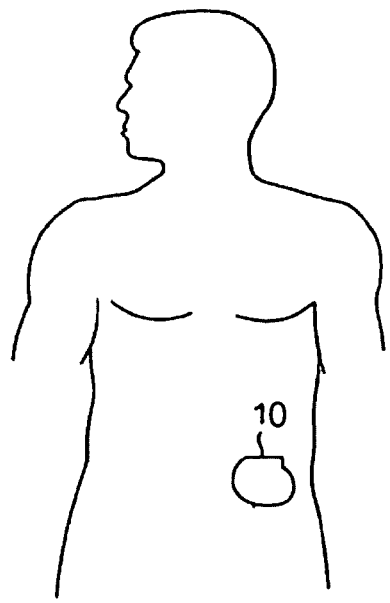
Figure 2D:
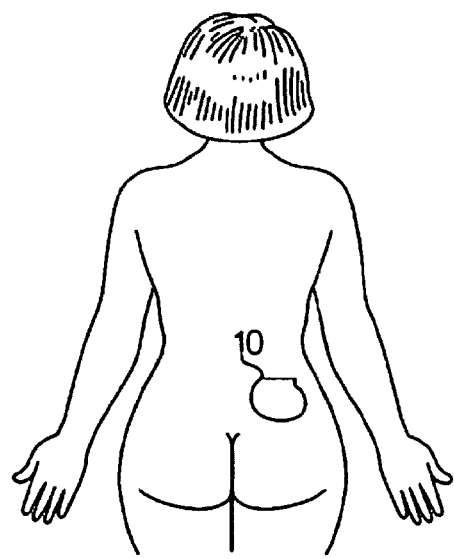

Referring to FIGS. 2A through 2D, alternative locations for implanting infusion device 10 are shown. As depicted in FIG. 2A, device 10 may be implanted in the pectoral region of a patient. Alternatively, infusion device 10 may be implanted in the head of a patient, more specifically behind the patient's ear (FIG. 2B), in the patient's abdomen (FIG. 2C) or in the patient's lower back or buttocks (FIG. 2D). Of course, infusion device 10 may be placed in any medically acceptable location in patient.

Figure 3:
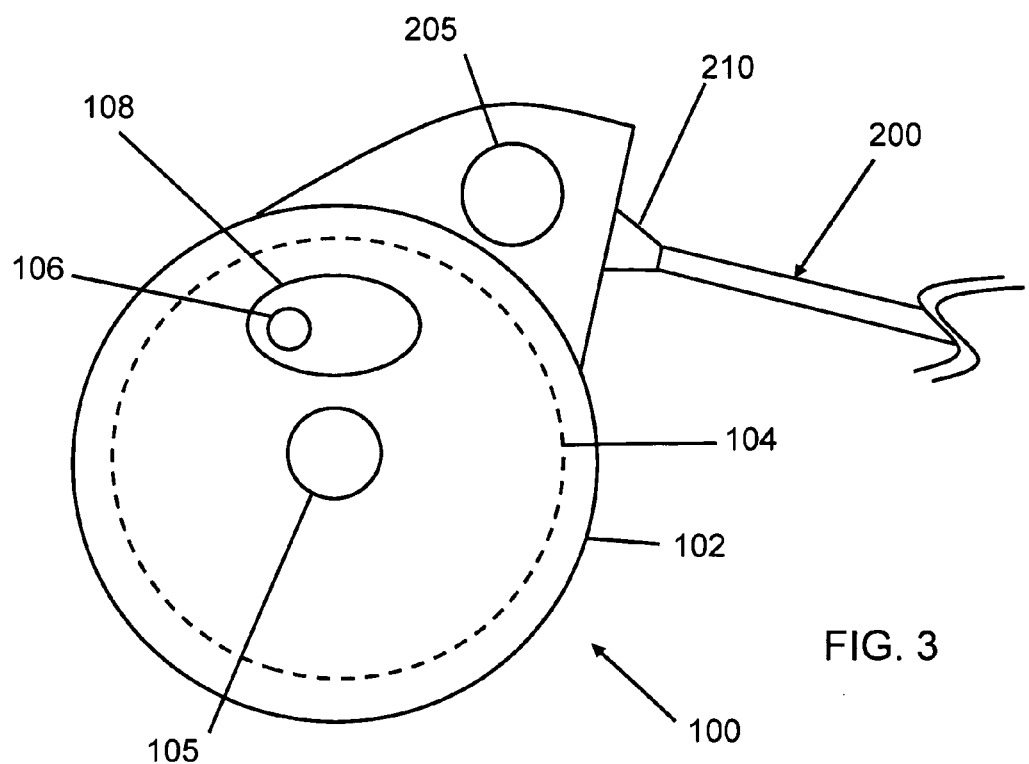
FIG. 3 is a schematic top view of an infusion system, specifically an infusion device connected to a catheter.

Referring to FIG. 3, an enlargement of a representative implantable infusion system is shown. This view is taken from the direction of the fluid reservoir looking toward the bulkhead housing the pump. Infusion device 100 has a bulkhead 102 (for example a hermetically sealed bulkhead 102) having a fluid reservoir 104 for containing fluid medication to be infused into a patient, fluid reservoir 104 indicated in dashed lines herein. Bulkhead 102 includes a refill port 105 in fluid communication with reservoir 104 which is operably coupled to a pump 108 via an inlet 106 into pump 108 from reservoir 104. Reservoir 104 usually has a large outlet therefrom (not illustrated), which typically occupies the entire area of reservoir 104. In some embodiments, there is usually no specific aperture that functions as an outlet but rather, fluid is free to exit reservoir 104 along the entire interface with bulkhead 102. Thus in this figure, the entire area of reservoir 104 is an outlet from reservoir 104 in fluid communication with pump inlet 106. Pump 108 can be an osmotic, peristaltic, or piston pump, or the like, which facilitates movement of the fluid from reservoir 104 via inlet 106.

In the illustrated embodiment, a catheter 200 is connected to infusion device 100 via a catheter connector 210. The depicted infusion device 100 also includes a catheter access port 205, which is in fluid communication with catheter 200. Fluid, e.g., fluid medication, may be injected into catheter access port 205, e.g. to deliver a bolus of therapeutic agent. Examples of infusion devices 100 having injection ports 105 in fluid communication with reservoirs 104 and having catheter access ports 205 include Medtronic, Inc.'s SynchroMed® series of infusion devices.

In some embodiments, infusion device 100 is referenced by the pressure acting on reservoir 104 within bulkhead 102. Infusion devices of this disclosure, such as infusion devices 10, 100, can be negative pressure devices, having the pressure in reservoir 104 less than or generally the same as the atmospheric pressure to which device 10, 100 was exposed to during filling operations. Fluid from a negative pressure reservoir 104 is drawn out by pump 108; the pressure within reservoir 104 is insufficient to expel fluid from reservoir 104. Typically, the pressure within a negative pressure reservoir is between about −5 psig and neutral, in relation to the environment surrounding reservoir 104, although other negative pressures might be used. In general, the negative pressure should not so low that the pump (e.g., pump 108) is unable to pull the fluid from the reservoir. In some device designs, the pressure may be slightly positive, for example, up to about 4.5 or about 5 psig; the pressure will generally not be above 6 psig. In some embodiments, the pressure within the pressure reservoir is between about −4.5 psig and neutral. In other embodiments, infusion devices can be neutral or positive pressure devices, having the pressure in reservoir 104 greater than the pressure within bulkhead 102 external to reservoir 104. Some infusion devices, such as those described by U.S. Pat. No. 4,838,887 (Idriss), have high positive pressure, of about 8 psig or greater. The infusion devices of this disclosure have a pressure within reservoir no greater than about 6 psig, and usually no greater than about 5 psig. In many embodiments, the pressure is no greater than 4.5 psig and in some embodiments, no greater than 1 psig. It should be understood that infusion devices in accordance with this disclosure may include additional components or may omit some of the components illustrated in FIGS. 1-3.

The infusion devices of this disclosure, whether negative pressure, neutral, or slightly positive pressure, include a bacterial filter in fluid communication with the reservoir (e.g., reservoir 104) and with the pump (e.g., pump 108) via its inlet aperture (e.g., inlet 106). The filter operates to prevent bacteria and other foreign matter from passing into the pump and into to the human body. Suitable filters are known to one of skill in the art. An example of suitable filter material is PTFE membrane, having a pore size of about 0.22 micrometers. The filter configuration of this disclosure inhibits the occurrence of "air lock" due to gas bubble formation in the fluid pathway. "Air lock" occurs when the presence of a gas bubble or multiple gas bubbles in the reservoir or elsewhere in the fluid path inhibits fluid (e.g., drugs or medicament) from passing through the filter and into the pump. Air lock usually occurs when the infusion device is tipped or tilted so that a bubble rises to the upper portion of the device, blocking the path of the fluid to the pump. This blockage usually occurs at the bacterial filter, because the bubble is not able to pass through the filter material or be moved from the fluid pathway. With negative pressure infusion devices and even with slight positive pressure infusion devices, the pressure exerted on the fluid by the pump is low and is typically unable to move the gas bubble in order to pull the fluid through the filter. Bubble formation generally does not occur in highly positive pressure reservoir devices (e.g., those having a reservoir pressure greater than about 6 psig or greater than about 8 psig), because even if formed, gas bubbles dissolve back into the fluid at high pressures. At least for this reason, bubble formation and air lock is not a problem in highly positive pressure reservoir infusion devices.

In accordance with this disclosure, the filter in the infusion device is configured to provide a fluid path for fluid medicament to be pulled from the reservoir to the pump, regardless of the orientation of the infusion device. The configuration of the filter provides a fluid path from the reservoir to the pump, even in the presence of a gas bubble. The filters of this disclosure are suitable for use in infusion devices having various configurations. For example, the outlet from the reservoir may occupy the general entire area covered by the filter, or may have specific or discrete apertures or outlets, of any shape or size, from the reservoir. The infusion device may have a single inlet aperture or a plurality of inlet apertures leading to the pump from the reservoir. The reservoir outlet may be aligned with or offset from the pump inlet. In accordance with this disclosure, any fluid from the reservoir will pass through a bacterial filter prior to reaching the pump inlet.

In some embodiments, the filter is annular, creating a continuous 360 degree fluid path exterior to the reservoir. See, for example, FIGS. 4A and 4B, which illustrate an annular filter in fluid communication with a single pump inlet. In other embodiments, the filter is semi-annular, being only a portion of an annulus (i.e., extending less than 360 degrees). The bacterial filter extends across the fluid flow path from the reservoir to the pump inlet and typically, the filter will create an available alternate fluid flow path of at least about 180 degrees between the reservoir and the pump. See, for example, FIG. 5A, which illustrates a semi-annular filter, in particular a filter extending about 180 degrees, in fluid communication with a single pump inlet aperture and FIG. 5B, which illustrates a semi-annular filter in fluid communication with a plurality of pump inlet apertures, both having a discrete reservoir outlet. A semi-annular filter is any length less than annular (i.e., less than 360 degrees), and will typically be between about 180 degrees and about 350 degrees, in some embodiments between about 200 degrees and about 290 degrees. In some embodiments, it may be preferred to have the filter larger than that needed to cover the pump inlet(s). For example, if there are two inlets positioned 180 degrees apart, the filter may be greater than 180 degrees, for example, about 200 degrees. As another example, if there are three inlets positioned over 270 degrees, the filter may be greater than 270 degrees, for example, about 290 degrees. Similarly, in some embodiments, it may be preferred to have the filter larger than that needed to cover the reservoir outlet(s).

Referring to FIG. 4A, a schematic top plan view of a portion of an infusion device 110 is illustrated. A cross-sectional side view of infusion device 110 is illustrated in FIG. 4B. Infusion device 110 has a bulkhead 112 and a reservoir 114 in fluid communication via reservoir outlet 118. In this rendition, bulkhead 112 and reservoir 114 are circular with the same diameter. A filter 115, specifically an annular filter (i.e., extending 360 degrees), is positioned (e.g., centered) between bulkhead 112 and reservoir 114, in this embodiment, sealed to bulkhead 112 via gaskets 119. Outlet 118 from reservoir 114 is a specific or discrete aperture, in this embodiment a rectangle; in other embodiments, the outlet may have other shapes or occupy the general entire area of filter 115. Also illustrated is an inlet 116 for operable connection to a pump (not illustrated). Any fluid exiting from the interior of reservoir 114 passes through outlet 118 and filter 115 prior to reaching inlet 116.

It is understood that although a circular bulkhead 112, a circular reservoir 114 and a centered annular filter 115 positioned between one inlet 116 and one outlet 118 are described and shown in FIGS. 4A and 4B, these characteristics are not limiting. For example, other embodiments may have differently shaped and/or sized bulkheads, reservoirs or filters. Other embodiments of infusion devices may have other numbers of, and different shapes and/or sizes of reservoir outlets and/or pump inlets.

Infusion device 110 is configured to function in generally any orientation. On occasion, infusion device 110 may be positioned in an orientation where a gas bubble, present in reservoir 114 enters outlet 118 and inhibits fluid flow to inlet 116. In many embodiments, the bubble is not able to pass through the filter material or be moved from the fluid pathway, particularly for neutral infusion devices, negative pressure infusion devices and slight positive pressure infusion devices. The fluid, however, is typically able to flow around the air bubble and pass through filter 115 at a location where the air bubble is not present. For example, referring to FIG. 4B, if an air bubble were present at outlet 118, fluid would be inhibited from passing directly through filter 115, i.e., at region "A". The fluid could, however, flow along the alternate path defined by filter 115, gaskets 119 and the bulkhead wall, pass through filter 115 at region "B", and thus flow to pump inlet 116.

FIG. 5A illustrates a schematic top plan view of a portion of another infusion device, having a bulkhead 122A and a reservoir 124A. A filter 125A, specifically a semi-annular filter extending about 180 degrees, is positioned between bulkhead 122A and reservoir 124A. Two outlets 128A, 128B from reservoir 122A, positioned approximately 160 degrees apart, are present below filter 125A. Also illustrated in FIG. 5A is an inlet 126 for operable connection to a pump (not illustrated). In FIG. 5A, any fluid from either outlet 128A, 128B of reservoir 124A passes through filter 125A prior to reaching inlet 126. If a direct path through filter 125A via either outlet 128A, 128B becomes blocked or occluded, fluid can flow through the other outlet to inlet 126 via the alternate path defined in part by filter 125A.

FIG. 5B illustrates an alternate embodiment of a schematic top plan view of a portion of an infusion device with bulkhead 122B, a reservoir 124B, and a filter 125B, specifically a semi-annular filter, positioned between bulkhead 122B and reservoir 124B. Filter 125B extends approximately 225 degrees. One outlet 128 from reservoir 124B is present below filter 125B. A plurality of inlets 126A, 126B for operable connection to a pump (not illustrated) are positioned 180 degrees opposite each other. In FIG. 5B, any fluid from outlet 128 of reservoir 124B passes through filter 125B prior to reaching either inlet 126A, 126B. If a direct path through filter 125B from outlet 128 becomes blocked or occluded, fluid can flow to inlet 126A, 126B via the alternate path defined in part by filter 125B.

Figure 6A:
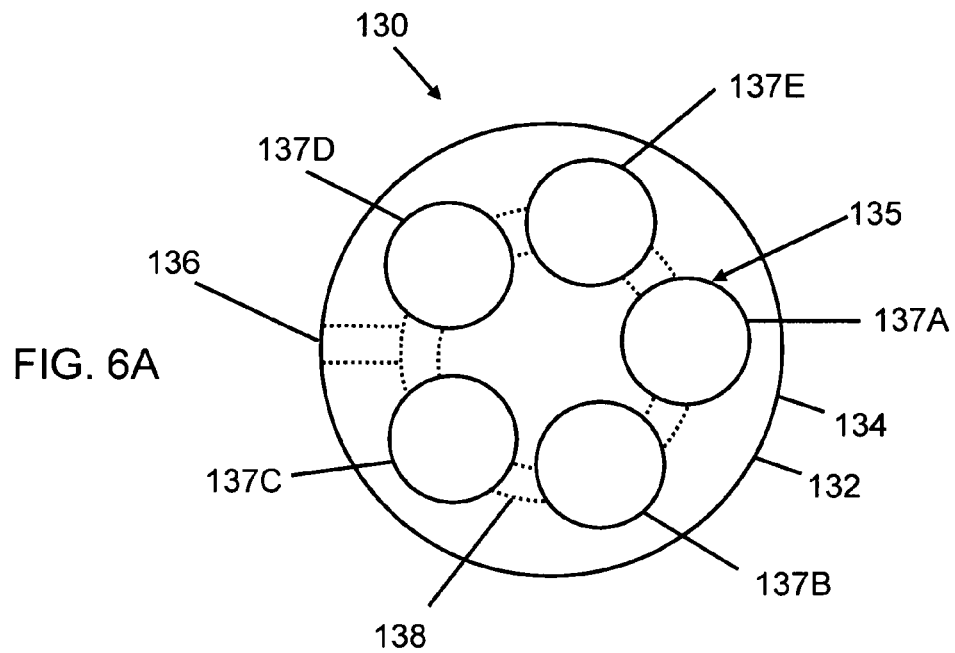
FIG. 6A is a schematic bottom view of an embodiment of an infusion device having a filter comprising a plurality of filter elements according to this disclosure.
Figure 6B:
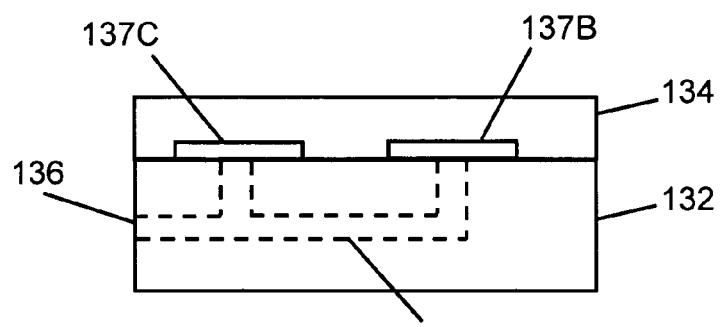
FIG. 6B is a schematic side view of the infusion device of FIG. 6A.

In some embodiments, the filter comprises a plurality of filter sections in fluid communication with each other. See, for example, FIG. 6A which illustrates a schematic bottom plan view of a portion of an infusion device; FIG. 6B is a side view of the device of FIG. 6A.

Infusion device 130 has a bulkhead 132 and a reservoir 134 in fluid communication. In this rendition, bulkhead 132 and reservoir 134 are circular with the same diameter. A filter 135 is positioned between bulkhead 132 and reservoir 134, in this embodiment, sealed to reservoir 134, for example by not shown gaskets. Filter 135 is composed of a plurality of individual filter elements, in this embodiment, five filter elements 137A, 137B, 137C, 137D and 137E. In this embodiment, filter elements 137A, 137B, 137C, 137D, 137E are discrete filter elements in fluid communication with each other via an internal passage 138 present within bulkhead 132 extending below each of the filter elements. Outlets(s) from reservoir 134 provide a fluid flow path from reservoir 134 to bulkhead 132 (specifically to internal passage 138), with filter 135, specifically filter elements 137A, 137B, 137C, 137D, 137E positioned across the fluid flow path. Internal passage 138 leads to a pump inlet 136 for operable connection to a pump (not illustrated). Any fluid from reservoir 132 passes through filter 135, specifically through at least one of filter elements 137A, 137B, 137C, 137D, 137E prior to reaching inlet 136. If a direct path through any of the elements, e.g., filter element 137A, becomes blocked or occluded, fluid can flow to inlet 136 via the path defined in part by the other filter elements, e.g., filter elements 137B, 137C, 137D, 137E and internal passage 138. In this embodiment, the path defined by filter elements 137B, 137C, 137D, 137E and internal passage 138 is annular; in some embodiments, the path may be at least about 180 degrees or at least about 270 degrees, or 360 degrees.

Various additional embodiments of infusion devices having a bacterial filter according to this disclosure are schematically illustrated in FIGS. 7 through 11 as block diagrams. It should be understood that features illustrated could be interchanged among the various schematic embodiments, and also among the previous embodiments of FIGS. 1 through 6B.

Figure 7:
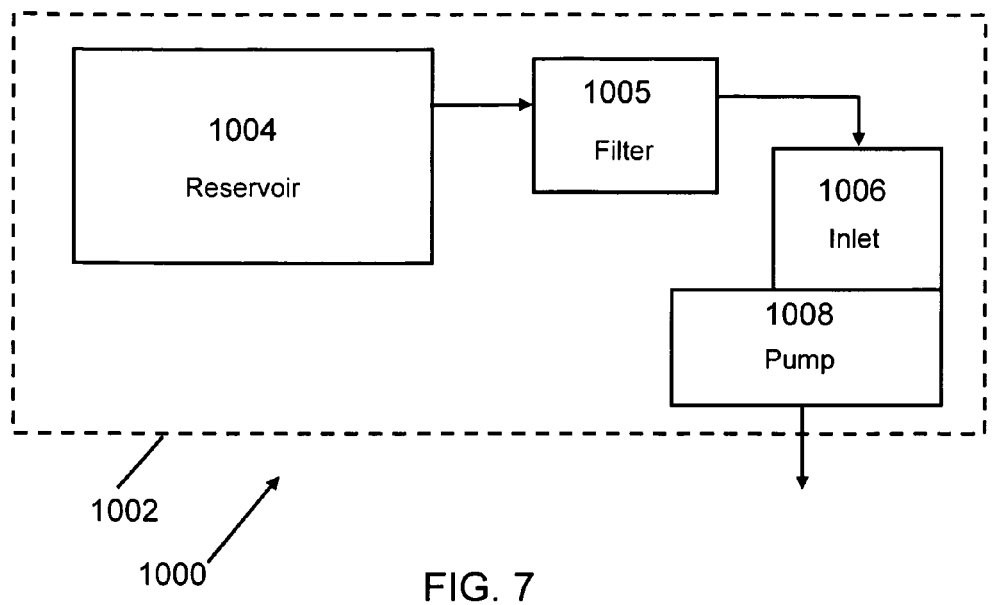
FIG. 7 is a schematic block diagram of an embodiment of an infusion device according to this disclosure.

In FIG. 7, an infusion device 1000 has a bulkhead 1002 including a fluid reservoir 1004 for retaining a fluid medication. Fluid medication exits reservoir 1004 via an outlet (not shown). Within bulkhead 1002 is also a pump 1008 having an inlet 1006. In fluid communication between reservoir 1004 and pump 1008 (particularly inlet 1006) is a filter 1005. If reservoir 1004 is a negative pressure reservoir, pump 1008 pulls the fluid medication from reservoir 1004 through filter 1005 and supplies it to the patient.

Figure 8:
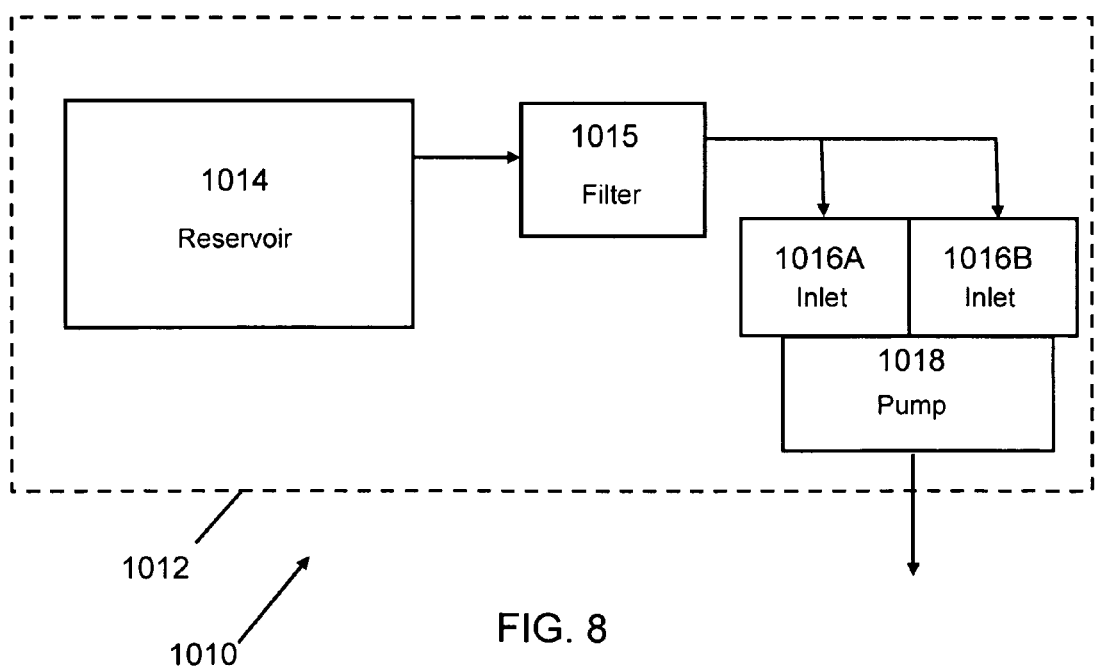
FIG. 8 is a schematic block diagram of an alternate embodiment of an infusion device according to this disclosure.

The schematic device of FIG. 8 differs from FIG. 7 in that the pump has a plurality of inlets. In FIG. 8, an infusion device 1010 has a bulkhead 1012 including a fluid reservoir 1014 for retaining a fluid medication. Within bulkhead 1012 is also a pump 1018 having a first inlet 1016A and a second inlet 1016B. In fluid communication between reservoir 1014 and pump 1018 (particularly inlets 1016A, 1016B) is a filter 1015. Pump 1018 pulls the fluid medication through filter 1015 and supplies it to the patient.

Figure 9:
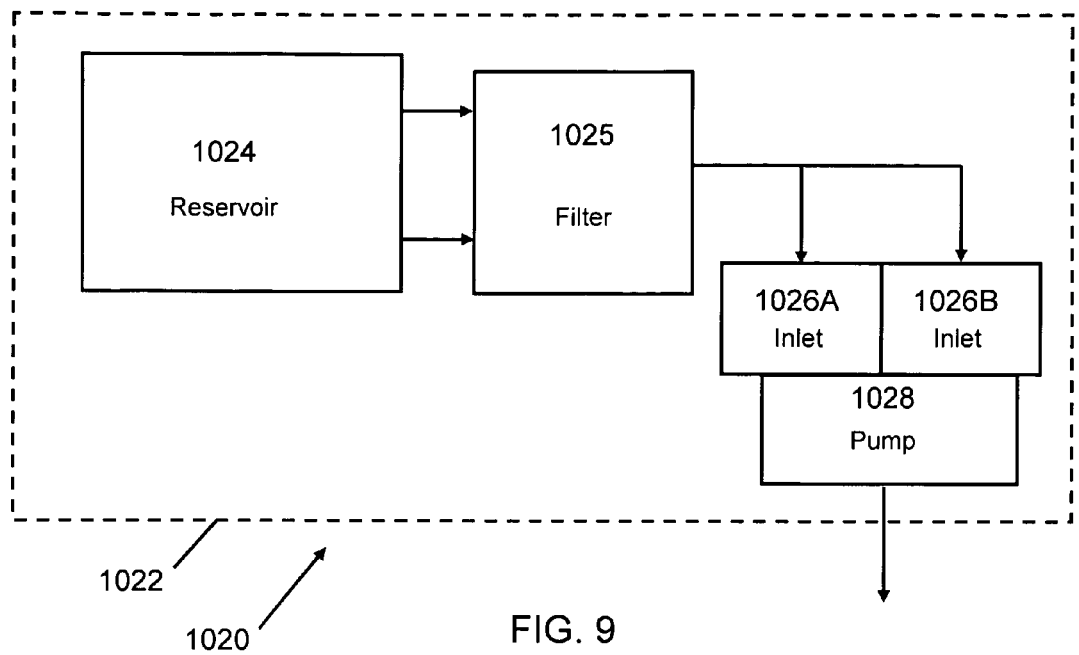
FIG. 9 is a schematic block diagram of another alternate embodiment of an infusion device according to this disclosure.

The schematic device of FIG. 9 differs from FIG. 7 in that the pump has a plurality of inlets. In FIG. 9, an infusion device 1020 has a bulkhead 1022 including a fluid reservoir 1024 for retaining a fluid medication. Within bulkhead 1022 is also a pump 1028 having a first inlet 1026A and a second inlet 1026B. In fluid communication between reservoir 1024 and pump 1028 (particularly inlets 1026A, 1026B) is a filter 1025. Pump 1028 pulls the fluid medication through filter 1025 and supplies it to the patient.

Figure 10:
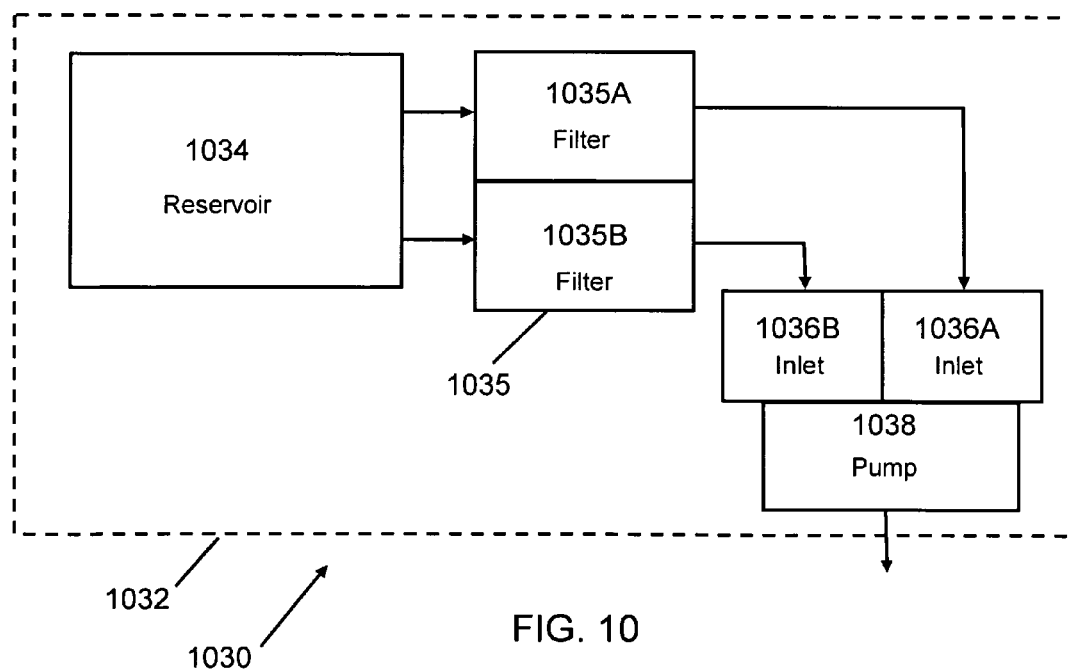
FIG. 10 is a schematic block diagram of yet another alternate embodiment of an infusion device according to this disclosure.

The schematic device of FIG. 10 is similar to that of FIG. 9 in that the pump has a plurality of inlets, but differs in that there are two filters in fluid communication between the reservoir and the pump. In FIG. 10, an infusion device 1030 has a bulkhead 1032 in which is fluid reservoir 1034 for retaining a fluid medication. Within bulkhead 1032 is also a pump 1038 having a first inlet 1036A and a second inlet 1036B. In fluid communication between reservoir 1034 and pump 103 is a filter 1035. Filter 1035 is composed of a plurality of filter elements, in this embodiment a first filter 1035A and a second filter 1035B. In this embodiment, filters 1035A, 1035B are in fluid communication with each other; that is, there is a fluid path between the filters. Pump 1038 pulls the therapeutic agent through filter 1035 and supplies it to the patient. As illustrated in FIG. 10, fluid from reservoir 1034 flows through filter 1035A to inlet 1036A and also from reservoir 1034 through filter 1035B to inlet 1036B. Because filters 1035A, 1035B are in fluid communication with each other, fluid initially passed to filter 1035A could flow through filter 1035B, for example, if filter 1035A were to be blocked by a gas bubble.

Figure 11:
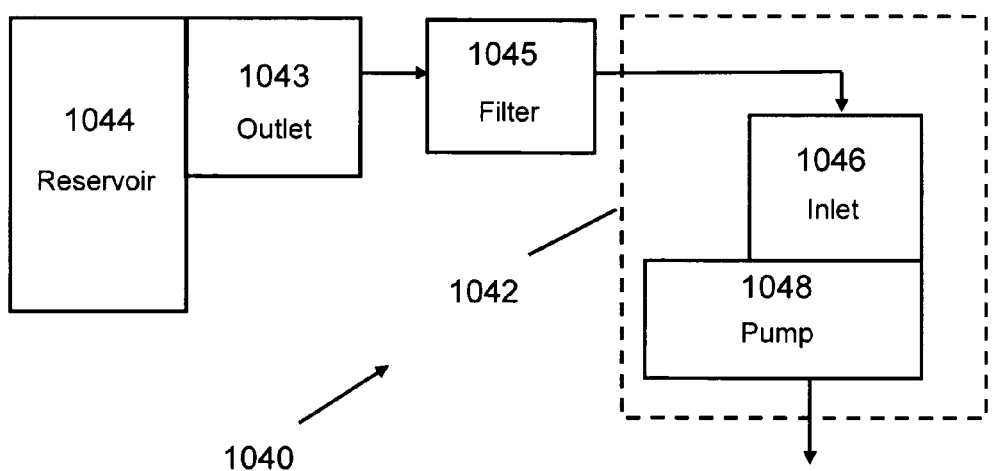
FIG. 11 is a schematic block diagram of still another embodiment of an infusion device according to this disclosure.

The previous examples have the common feature of having the reservoir within the bulkhead or housing of the infusion device. In some device designs, the supply of fluid medication is separate from the bulkhead. FIG. 11 schematically illustrates an alternate configuration for an infusion device according to the present disclosure. In this device, the reservoir is external to the bulkhead. In FIG. 11, an infusion device

1040 has a bulkhead 1042 retaining a pump 1048 having an inlet 1046. External to bulkhead 1042 is a reservoir 1044 with an outlet 1043 for supplying fluid medication to pump 1048. An example of an external reservoir is a flexible bladder. In fluid communication between external reservoir 1044 (particularly outlet 1043) and pump 1048 (particularly inlet 1046) is a filter 1045.

The above schematic embodiments provide various configurations of negative pressure, neutral, and slightly positive pressure infusion devices that have a bacterial filter of at least about 180 degrees. With such a filter configuration, no matter what orientation of the infusion device, the inlet to the pump will be in fluid communication with the outlet from the reservoir, due to the alternate fluid flow path formed by the bacterial filter. The infusion device will not be subject to air lock caused by a gas bubble blocking the path from the reservoir to the pump.

Thus, numerous embodiments of the IMPLANTABLE INFUSION DEVICE HAVING FILTER have been disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable infusion device comprising:
   a reservoir comprising an interior having a pressure of no more than about 5 psig;
   a bulkhead defining an annular passage in fluid communication with the reservoir interior, the bulkhead further housing a pump having an inlet, the inlet in fluid communication with the reservoir interior via the annular passage; and
   a bacterial filter positioned between the reservoir interior and the annular passage.

2. The device of claim 1, further comprising a plurality of reservoir outlets in fluid communication with, and between, the reservoir interior and the annular passage.

3. The device of claim 1, wherein the bacterial filter extends at least about 180 degrees of the annular passage, wherein the filter is positioned to filter fluid flowing through each of the plurality of reservoir outlets.

* * * * *